(12) United States Patent  (10) Patent No.: US 9,340,596 B2
Hua et al.  (45) Date of Patent: May 17, 2016

(54) FUSION PROTEIN COMPRISING TUMOR NECROSIS FACTOR RELATED APOPTOSIS INDUCING LIGAND AND INTEGRIN LIGAND AND USE THEREOF

(75) Inventors: Zichun Hua, Nanjing (CN); Lin Cao, Nanjing (CN)

(73) Assignee: NANJING UNIVERSITY (CN)

( * ) Notice: Subject to any disclaimer, the term of this patent is extended or adjusted under 35 U.S.C. 154(b) by 563 days.

(21) Appl. No.: 12/739,003

(22) PCT Filed: Oct. 8, 2008

(86) PCT No.: PCT/CN2008/001675
§ 371 (c)(1),
(2), (4) Date: Apr. 21, 2010

(87) PCT Pub. No.: WO2009/065292
PCT Pub. Date: May 28, 2009

(65) Prior Publication Data
US 2010/0311948 A1  Dec. 9, 2010

(30) Foreign Application Priority Data

Oct. 23, 2007  (CN) .......................... 2007 1 0133862

(51) Int. Cl.
*C07K 19/00* (2006.01)
*C07K 14/52* (2006.01)
*C07K 14/47* (2006.01)
(Continued)

(52) U.S. Cl.
CPC ......... *C07K 14/4747* (2013.01); *C07K 14/7151* (2013.01); *A61K 38/00* (2013.01)

(58) Field of Classification Search
None
See application file for complete search history.

(56) References Cited

U.S. PATENT DOCUMENTS 6,284,263 B1 * 9/2001 Place
6,479,260 B1 * 11/2002 Takayama et al.
6,521,228 B1   2/2003 Wiley et al.
(Continued)

FOREIGN PATENT DOCUMENTS

CN   1614025    5/2005
CN   101157729  4/2008
(Continued)

OTHER PUBLICATIONS

Matsuda et al., Engue virus-induced apoptosis in hepatic cells is partly mediated by Apo2 ligand/tumor necrosis factor-related apoptosis-inducing ligand, J. Gen. Virol. 86:1055-1065, 2005.*

(Continued)

*Primary Examiner* — Claire Kaufman
(74) *Attorney, Agent, or Firm* — Schmeiser, Olsen & Watts, LLP

(57) ABSTRACT

Provided is a fusion protein comprising a tumor necrosis factor related apoptosis inducing ligand (TRAIL), integrin ligands of $\alpha V\beta 3$ and $\alpha V\beta 5$ and a linking peptide. Also provided are the expression method and simple separation and purification process for the production of the fusion protein which is soluble and has high content of the polymer, and use of the fusion protein for the manufacturing of a medicament for the treatment of tumor. The fusion protein has good tumor tissue targeting property, significantly enhanced anti-tumor effect, which can also reduce the dose of the needed protein for the target treatment effect, improve the bioavailability, reduce the treatment cost, decrease and overcome the potential toxic and side effects of the tumor necrosis factor-related apoptosis inducing ligand.

5 Claims, 3 Drawing Sheets

(51) Int. Cl.
*C07K 14/715* (2006.01)
*A61K 38/00* (2006.01)

(56) References Cited

U.S. PATENT DOCUMENTS

| | | | |
|---|---|---|---|
| 6,797,493 | B2 * | 9/2004 | Sun et al. |
| 6,864,359 | B1 * | 3/2005 | Luo |
| 2001/0046498 | A1 | 11/2001 | Ruoslahti |
| 2003/0185845 | A1 * | 10/2003 | Klysner et al. |
| 2004/0265300 | A1 | 12/2004 | Edelman et al. |

FOREIGN PATENT DOCUMENTS

| | | |
|---|---|---|
| WO | WO 03038043 A2 * | 5/2003 |
| WO | 2007/011217 | 1/2007 |

OTHER PUBLICATIONS

Wu et al., Induction of potent TRAIL-mediated tumoricidal activity by hFLEX/Furin/TRAIL recombinant DNA construct, Mol. Ther. 9(5):674-681, 2004.*

Granger et al., Tumor targeting with RGD peptide ligands-design of new molecular conjugates for imaging and therapy of cancers, Anti-Cancer Agents Med. Chem. 7:552-558, Sep. 2007.*

Verrier et al., Function of linear and cyclinc RGD-cointaining peptides in osteoprogenitor cells adhension process, Biomaterials, 23:585-596, 2002.*

Jacob et al., Suppression of pantcreatic tumor growth in the liver by systemic administration of the TRAIL gene driven by the hTERT promoter, Can. Gene Ther. 12:109-115, 2005.*

Curnis et al. Coupling tumor necrosis factor-alpha with alpah-v integrin ligands improves its antineoplastic activity, Cancer Res. 64:565-571, Jan. 15, 2005.*

Lhadenranta et al., Treatment of hpoxia-induced retinopathy with targeted proapoptotic peptidomimetic in a mouse model of disease, FASEB J. 21:3272-3278, Oct. 1, 2007.*

Campbell, N.A., Biology (The Benjamin/Cummings Publishing Co. Inc.:Menlo Park CA), p. G-9, 1987.*

Zhao, L. H et al. Cloning, expression and purification of RGD-s TRAIL and its anti-tumor effects in vitro. Letters in Biotechnology, 15(3): 226-230, May 2004, full English translation.*

Yeow et al., Cytotoxic gene therapy of esophageal cancers using the recombinant RGD-modified adenovirus expressing membrane-bound TRAIL (TNF-Related Apoptosis-Inducing Ligand): an in vitro and in vivo analysis, Proc. Amer. Assoc. Cancer Res. 47:Abst. 2994, Apr. 2006.*

Schein, C., Production of soluble recombinant proteins in bacteria, BioTechnology, 7(11):1141-1149, 1989.*

Koivunen et al., Phage libraries displaying cyclic peptides with different ring sizes: ligand specificities of RGD-directed integrins, Bio/Technol. 13:265-270, 1995.*

Creightron, T.E., Proteins:Structures and Molecular Properties, New York: W.H. Freeman and Comp., p. 8, 1984.*

Amersham Pharnacia Biotech (2000) The Recombinant Protein Handbook: Protein Amplification and Simple Purification, AA Edition, Amersham Pharmacia Biotech AB:Sweden, 2000.*

Potts, J.T., Molecular biology of the parathyroid hormone: biological actions, Clin. Case Min. Bone Metab. 1(2):93-98, 2004.*

Ye et al., Structure of calmodulin bound to a calcineurin peptide: a new way of making an old binding mode, Biochem. 45(3):738-745, 2006.*

Zhao, L. H et al. Cloning, expression and purification of RGD-s TRAIL and its anti-tumor effects in vitro. Letters in Biotechnology. May 2004, vol. 15, No. 3, pp. 226-230.

Cao, L. et al Enhancement of antitumor properties of TRAIL by targeted delivery to the tumor neovasculature. Mol Cancer Ther. Apr. 2008, vol. 7, No. 4, pp. 851-861.

Tarrua, M. et al. RGD-avidin-biotin pretargeting to avb3 integrin enhances the proapoptotic activity of TNFa related apoptosis inducing ligand (TRAIL). Apoptosis. Feb. 2008, vol. 13, No. 2, pp. 225-235.

* cited by examiner

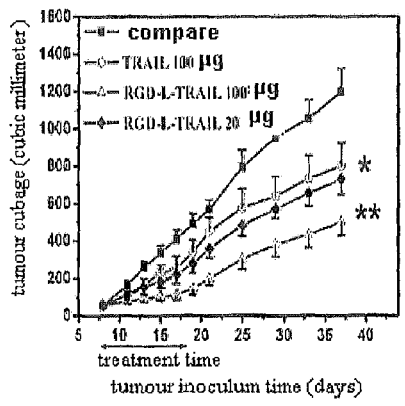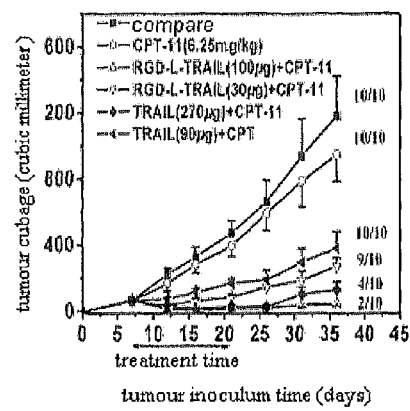
FIG. 6
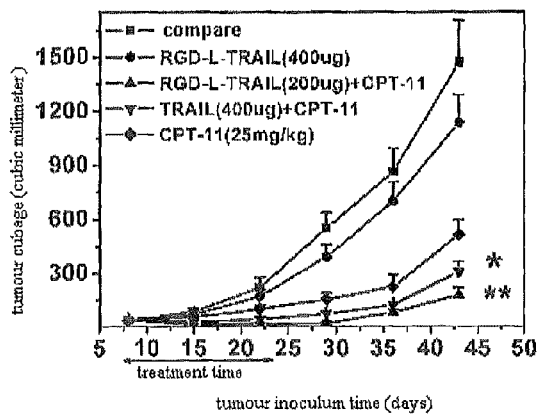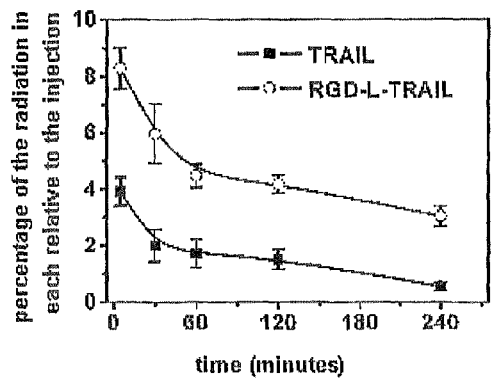
FIG. 7
FIG. 8

FUSION PROTEIN COMPRISING TUMOR NECROSIS FACTOR RELATED APOPTOSIS INDUCING LIGAND AND INTEGRIN LIGAND AND USE THEREOF

FIELD OF THE INVENTION

This present invention relates to the biotechnological field.

BACKGROUND OF THE INVENTION

Tumor necrosis factor-related apoptosis-inducing ligand (TRAIL) is a member of the tumor necrosis factor superfamily. Similar to other members of the tumor necrosis factor superfamily, soluble TRAIL forms a homotrimer, which cross-links three receptor molecules on the surface of target cells, thus inducing the biological functions. The apoptosis inducing function of TRAIL is realized by its interaction with the death receptor 4(DR4) and DR5 on the tumor cells through death signal transmission. Although other members of tumor necrosis factor superfamily are restricted due to their systemic side effects, TRAIL is a relatively safe agent for cancer-specific therapy. TRAIL induces apoptosis in a variety of tumor cells and cancer cells in vitro, and shows substantial anti-tumor activity in rodent xenograft models, including colon cancer, breast cancer, multiple myeloma, glioma, prostate cancer and many other models. Particularly important, when drugs were administered to mice and non-human primates, TRAIL presented little or no toxicity. For the above reasons, recombinant TRAIL has been used in clinical trials for tumor treatment. However, some recent reports showed that, in addition to inducing tumor cell apoptosis, TRAIL is also involved in innate immunity and adaptive immunity, associated with autoimmune diseases. For example, recent studies have reported that TRAIL can regulate the negative selection or apoptosis of thymus cells during the thymus development process, and plays an important role in inducing autoimmune diseases such as type I diabetes. In addition, TRAIL receptors are extensively expressed in the whole body, and TRAIL also plays a role in liver cell death and hepatitis. Therefore, repeated and systemic use of high-dose exogenous TRAIL may lead to unforeseen immunological effects in clinic. As a result, there are serious concerns about the potential side effects of repeated and systemic use of TRAIL. Thus, there exists a need for a compound, method of preparation, and method of application of a TRAIL fusion protein which avoids the above mentioned deleterious side effects of wild-type TRAIL.

SUMMARY OF THE INVENTION

To overcome the shortcomings of wild-type TRAIL, the object of the following is to produce a fusion protein variant of TRAIL which specifically targets the tumor tissues, thus enhancing the efficacy of TRAIL, and reducing its side effects.

To achieve the aforementioned purpose, in the present disclosure, a fusion protein comprising a tumor necrosis factor related apoptosis inducing ligand (TRAIL), integrin ligands of αVβ3 and αVβ5 and a linking peptide is constructed. This is accomplished via regular gene engineering methods, that is to say, artificial synthesis or cloning of TRAIL coding genes, soluble expression of the genes, and simple separation and purification of the resulting protein.

Another aspect of this invention is αVβ3 and αVβ5 integrin ligands that are a short peptide containing an RGD sequence.

Further, the integrin ligands of αVβ3 and αVβ5 can also be a peptide containing an RGD sequence with a ring-handle structure, such as the short peptide ACDCRGDCFC (SEQ ID NO:1).

The sequence listing containing all the disclosed sequence IDs has been submitted as a separate text file, and is hereby incorporated by reference in its entirety. The name of the text file is 6798_Sequence_Listing.txt. The file was created on Jul. 12, 2012, and is 2 KB in size. Further, the integrin ligands of αVβ3 and αVβ5 are bound with the TRAIL through a binding peptide, and the binding peptide contains 2-20 amino acid residues.

Yet another aspect of this invention is the application of the fusion protein variant of TRAIL comprising integrin ligands of αVβ3 and αVβ5 and TRAIL in tumor treatment.

Yet another aspect of this invention is the combined application of the TRAIL fusion protein variant and the existing chemotherapy, radiation therapy, TCM treatment, biological treatment methods in the treatment of tumors.

Yet another aspect of this invention is the method of soluble expression and simple separation and purification process to achieve a high content of TRAIL and the polymers of its variants in *E. coli*. Although the expression products of TRAIL in *E. coli* mainly are the inclusion body products without biological activity, in the fusion protein variant of TRAIL, the molecular structure is more complicated, and molecular weight is greater than the wild-type of TRAIL. Therefore, when expressed in *E. coli*, there will be a greater formation of inclusion bodies, and the purification process will be more complicated. In the present invention, the cultivation and expression of TRAIL are carried out at low temperatures (10° C.-35° C.), which effectively avoids the formation of inclusion bodies.

Additionally, the use of chelation, metal affinity chromatography and ion-exchange chromatography, TRAIL and its variants have been effectively purified, resulting in a high purity of protein products. The purified products have a high proportion of polymerized TRAIL, and therefore, present very good biological properties.

The αVβ3 and αVβ5 integrins are minimally expressed in resting and normal vascular cells; however, in many tumor cells (such as melanoma, colon cancer, breast cancer and uterine cancer) and tumor endothelial cells, their expression is significantly increased. The TRAIL variants comprising integrin ligands of αVβ3 and αVβ5 can significantly enhance the distribution of TRAIL to tumor tissues through the targeted distribution of TRAIL to the tumor tissues, thus greatly enhancing the anti-tumor effects of TRAIL, while simultaneously significantly reducing the required dose of TRAIL.

Compared to current forms of TRAIL and its variants, the present invention has the following distinct characteristics:

(1) Better targeting of tumor tissues: previously existing forms of TRAIL accomplish selection of tumor tissues mainly by recognition of the death receptors DR4 and DR5 expressed in the tumor tissues. However, in the present invention, the TRAIL variant, in addition to the use of DR4 and DR5 expressed in tumor tissues, also makes use of the rich expression of αVβ3 and αVβ5 integrins in the tumor tissues, thus effectively realizing the improved targeted delivery of TRAIL to tumor tissues.

(2) More efficient anti-tumor effects: because of the targeted delivery of TRAIL to tumor tissues, the TRAIL variant in the present invention, compared with the same dose of previously existing forms of TRAIL, presents better anti-tumor effects regardless of whether it is used individually or combined with chemotherapy, radiotherapy, TCM treatment, biological treatment or other methods.

(3) Lower application dose because the TRAIL variant has better anti-tumor effects compared with the same dose of previously existing forms of TRAIL, when used, it can significantly reduce the dose required to achieve the same anti-tumor curative effect. The decreased dose of TRAIL variant protein will be able high efficiency, reduce the potential side effects, and reduce the expenses of tumor treatment.

(4) Convenient for expression and production: differing from the tumor-cell specific antibody and antibody-fragment targeting TRAIL fusion protein, in the present invention, the fusion of the TRAIL and the short-peptide ligand of integrins αVβ3 and αVβ5 slightly increases the molecular weight. This improves gene cloning, expression and production of the presently disclosed TRAIL variant, while realizing higher yields.

(5) Soluble expression and simple separation and purification: although TRAIL can form non-biologically active inclusion bodies when expressed in *E. coli*, in the present invention, the molecular structure and molecular weight of the TRAIL variant results in increased formation of inclusion bodies, which makes its purification more complicated. In the present invention, the cultivation and expression of TRAIL are carried out at low temperatures, which effectively avoids the formation of inclusion bodies. Additionally, through the use of chelation, metal affinity chromatography and ion-exchange chromatography, TRAIL and its variants have been effectively purified, resulting in a high purity of protein products. The purified products have a high proportion of polymerized TRAIL, therefore, they present very good biological properties. The present invention also provides a method of expression and a purification process to effectively express and purify a high proportion of polymerized TRAIL and its variants.

1A. SDS-PAGE analysis results: 1: molecular weight standard; 2: human TRAIL; 3. Human TRAIL variant;

1B. Non-reducing and non-denaturing PAGE analysis results: 1: Human TRAIL; 2: Human TRAIL variant.

Figure 2:
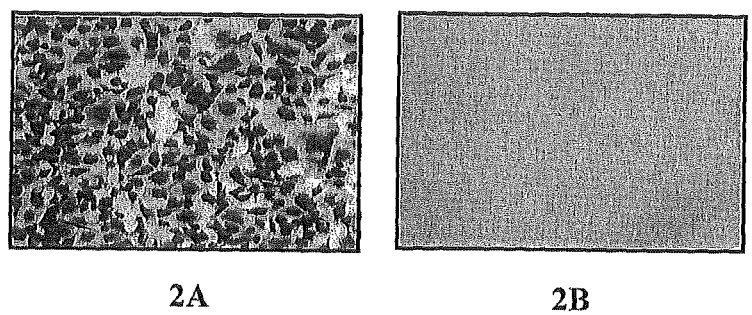

FIG. 2 Test of promotion of human foreskin microvascular endothelial cell adhesion and well-adhesion capability by human TRAIL variant (Zoom 200).

2A. Human foreskin microvascular endothelial cell adhesion to wells coated with human TRAIL variant at 6.4 µg/ml per well;

2B. Human foreskin microvascular endothelial cell adhesion to wells coated with human TRAIL at 6.4 µg/ml per well.

Figure 3:
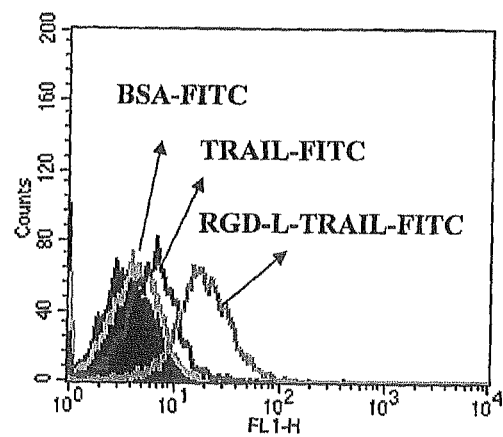

FIG. 3 Analysis of the in vivo binding of green fluorescein-labeled human TRAIL or its variant with tumor tissue in tumor animal models with a flow cytometer.

Tumor animal models: BALB/c nu/nu nude mice inoculated with COLO-205 tumor cells. Tail vein injection of human TRAIL variant RGD-L-TRAIL-FITC (black ash line, hollow peak chart), human TRAIL-FITC (black line, hollow peak chart), control protein BSA-FITC (light gray line, hollow peak chart) into tumor-bearing mice; after 30 min, the tumor tissues are peeled off to prepare cell suspension for analysis with a flow cytometer. The negative controls (black solid peak chart) are selected from the tumor animals without injection of any proteins.

Figure 4:
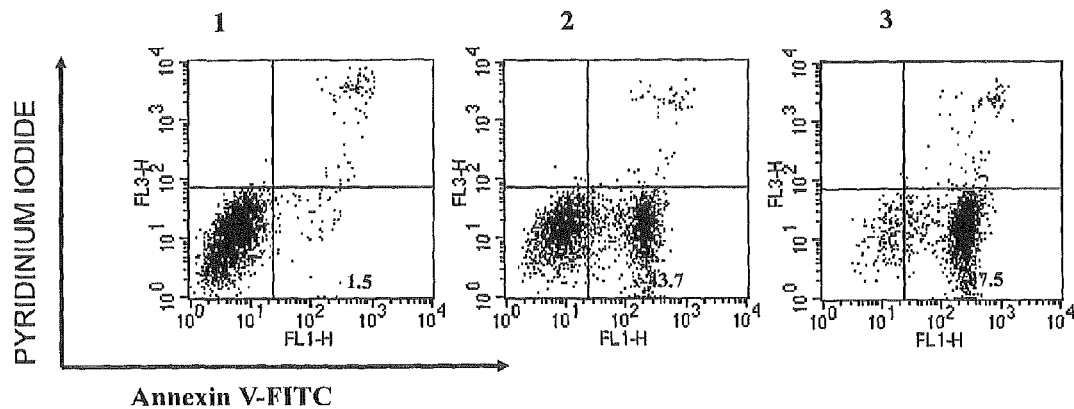

FIG. 4 Test of the capacity of inducing COLO-205 apoptosis of human TRAIL and its variant (2.43 ng/ml) with Annexin V and pyridine iodide (PI) double staining method.

1: control; 2: human TRAIL; 3: human TRAIL variant.

Figure 5:
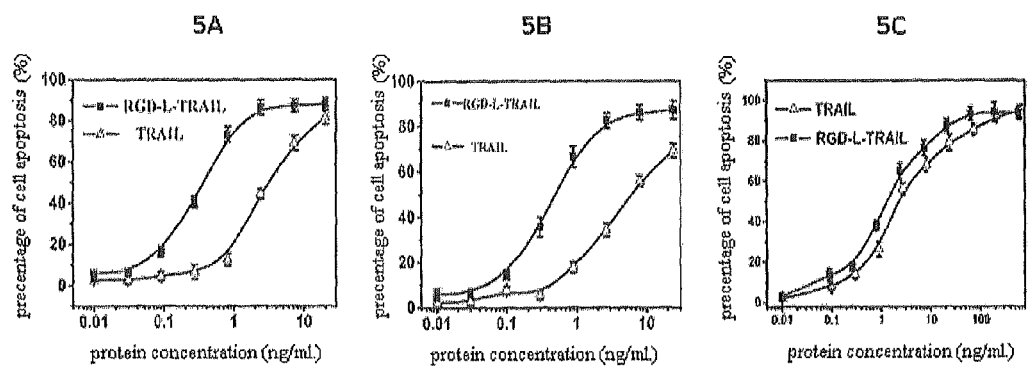

FIG. 5. Analysis of the dose-effect relationship of human TRAIL and its variant induced tumor cell apoptosis.

5A: COLO-205 cell; 5B: Jurkat cell; 5C: MDA-MB-231 cell.

FIG. 6 Individual treatment of human TRAIL and its variant in the COLO-205 tumor model and anti-tumor effect combined with CPT-11.

6A: Individual treatment of human TRAIL and its variants; 6B: CPT-11 combined treatment with human TRAIL and its variant. The data analysis results are represented with the average; the variance is the standard error; * indicates $p<0.05$; ** indicates $p<0.01$.

FIG. 7 Individual treatment of human TRAIL and its variant in the HT-29 colon tumor models and anti-tumor effect combined with CPT-11.

Statistical analysis results are represented by average value; the variance is the standard error; * indicates $p<0.05$; ** indicates $p<0.01$.

FIG. 8 Analysis of the targeting accumulation effect of human TRAIL and its variant in the tumor tissues of COLO-205 tumor animal models.

Separate injection from tail veins of 100 µl containing 5 Ci of 125I-labeled human TRAIL or its variant protein into the COLO-205 tumor bearing nude mice. 5, 30, 60, 120 and 240 minutes after injection, the tumor tissues were peeled off separately and weighed, and the radiation amount of the tumor tissues were measured with a liquid scintillation counter. The amount of radiation in the tumor tissues is represented by the percentage of measuring radiation quantity per gram of tissues and the injected radiation quantity (% ID/g). The results are the average value of three independent tests.

DETAILED DESCRIPTION OF THE INVENTION

Example (1) Gene Cloning, Expression and Purification of TRAIL Variant

The wild-type human TRAIL genes are obtained from reverse transcription of messenger RNA available from human placenta. The PCR primers for the gene for the TRAIL variant fused with the short peptide and ACDCRGDCFC (SEQ ID NO:1) are:

```
Primer 1:                                 (SEQ ID NO: 3)
5'-TGCAGATCATATGGCATGCGACTGCCGTGGTGA CTGCTT
and

CTGCGGTGGTGGTGGTGGTGTGAGAGAAAGAGGTCCTCAG-3';

Primer 2:                                 (SEQ ID NO: 4)
5'-ATGGATCCTTAGCCAACTAAAAAGGCCC-3'
```

The RGD-L-TRAIL gene for the short peptide ACDCRGDCFC (SEQ ID NO:1) and the connecting peptide of five glycines was obtained through PCR reaction. RGD-L-TRAIL gene was cloned to Novagen's pET-23a expression vector. The resulting recombinant expression plasmids were expressed in the *Escherichia coli* BL21 (DE3). To obtain soluble expression of RGD-L-TRAIL, the expression conditions should be as follows: The overnight growth of recombinant expression bacteria were diluted 100 times in the LB medium, and cultivated for 2.5 h at 37° C., and then cultivated for 1-2 h at 24° C. Under the condition of 24° C., IPTG was added to 0.6 mM, and then the bacteria were induced for expression at 24° C. overnight. After centrifugation, the bacteria were suspended in lysis buffer (50 mM sodium phosphate, 0.5 M NaCl, 1 mM dithiothreitol, pH 7.6) and lysed through ultrasonication. After separation and purification of RGD-L-TRAIL protein through Ni-NTA agarose gel medium (Qiagen Company), 60 mM imidazole elution peak was collected, and then purified through SP-Sepharose cation resin. In the test, all the water used is ultra-pure, endotoxin-free water. The protein quantitative measurement was carried out with the BCA protein test kit provided by Nanjing Jiancheng Bio-engineering Institute. The purity and molecular weight of TRAIL and its variant protein should be analyzed by the silver-staining SDS-PAGE method, and the molecular weight was determined by mass-spectrometry with Applied Biosystems 4700 Proteomics Analyzer.

(2) Cell Adhesion Assay of Human Foreskin Microvascular Endothelial Cells

The TRAIL and its variant protein are coated on a 96-well PVC plate overnight at 4° C. The coated 96-well plate was rinsed with 0.9% physiological saline, and then blocked for 1 h at 1640 culture medium containing 2% bovine serum albumin, and then rinsed again. After the human foreskin microvascular endothelial cells were digested, washed three times with phosphate buffer and re-suspended into the complete RPMI1640 medium, it was then added to the 96-well plate coated with TRAIL and its variant (40,000 cell per well). After the cells were incubated for 1.5 hours in an incubator containing 5% carbon dioxide, they were washed three times with physiological saline to remove the non-adherent cells. The adherent cells were fixed for 30 min with phosphate buffer solution (pH 7.3) containing 4% formalin and 2% sucrose, and then stained with 0.5% crystal violet. The fixed stained cells were rinsed several times, then dissolved with 100 ml DMSO to test the absorbance values at 540 nm. All the tests should be carried out at least three times independently.

(3) Binding Assay of TRAIL and its Variant with Endothelial Cells

The TRAIL and its variant were labeled with fluorescein (Sigma company), and the labeled proteins were separated from free fluorescein through a Sephadex-G25 size exclusion column. After human foreskin microvascular endothelial cells were digested by trypsin, washed twice with ice-cold phosphate buffer containing 2% fetal calf serum, and then re-suspended, they were added with 1 μg of labeled protein for incubation for 1 h at 4° C. The fluorescent-labeled bovine serum albumin was used as a control of the test. After being washed three times, the binding capacity of the stained cells was analyzed with a flow cytometer (Becton Dickinson Company).

(4) Analysis of Integrin αVβ3 and αVβ5 Expression Abundance

The cell surface integrin expression abundance was tested with a flow cytometer through the indirect labeling method. After digestion, the cells were rinsed twice with ice-cold phosphate buffer containing 2% fetal calf serum, re-suspended, and coated with one of the following monoclonal antibodies for 1 h on ice: anti-human αVβ3 integrin antibody MAB 23C6 (eBioscience, Inc.), or anti-human αVβ5 integrin antibody MAB 1961 (Chemicon International Inc.). purified mouse immunoglobulin G isotype (eBioscience Corporation) was used as a negative control. The cells coated with the first antibody were washed twice, added with green fluorescein conjugated goat anti-mouse immunoglobulin G1 (γ) (Caltag Laboratories Inc.) as a secondary antibody, and then reacted for 30 min-in the dark. They were then washed three times, fixed with phosphate buffer containing 4% formalin, and finally the integrin expression abundance was tested on the flow cytometer. All the staining tests should be repeated three times.

(5) Test of Cell Apoptosis with Annexin V and Pyridine Iodide (PI) Double Staining Method After the cells treated with TRAIL and its variant were digested with trypsin, they were removed from the cultivation plate, washed twice with phosphate buffer solution, and centrifuged for 5 min at 300 g centrifugal force. The supernatants were removed, and the cells were re-suspended in 100 ul of binding buffer solution. Then, Annexin V-FITC (BD Pharmgen) was added until a final concentration of 2 μg/ml was achieved, followed by incubation at room temperature. After 10 min, 400 ul of binding buffer was added, and the cells were transferred to a flow analysis tube. 1 μg of iodide-pyridine (Sigma Corporation) was added to each tube. The cells were analyzed with a flow cytometer within 30 min. At least three separate tests should be carried out for each cell line.

(6) Caspase-8 and Caspase-3 Activity Assay

Caspase-8 and Caspase-3 activity were determined by fluorescence detection kit (Oncogene Inc.). The test methods followed the methods provided by the factory protocol. The fluorescence values were tested with a microplate reader. The fluorescence parameters were as follows: excitation wavelength: 400 nm; emission wavelength: 505 nm.

(7) Test of Anti-Tumor Efficacy on Tumor Animal Models 5-6 week-old female nude mice were purchased from Shanghai Experimental Animal Center. The nude mice were injected through their tail veins with 100 μg of a specific antibody, i.e., purified Asialo GM-1 antibody (Wako Chemicals Inc., Japan) that blocks natural killer cells. After 24 hours, the upper right sides of the back of the nude mice were inoculated subcutaneously with 100,000 COLO-205 or HT-29 colon cancer cells. When the tumors reached 70 mm3, random grouping and treatment began. The recombinant TRAIL and its variant proteins were administered intraperitoneally, once daily for 10-14 days. The water-soluble camptothecin CPT-11 (11-hydroxy-camptothecin; Product Name: Irinotecan Hydrochloride Injection; Pharmacia/Upjohn Company's product) was administered intravenously once a week, two times in total. The recombinant proteins and camptothecin were diluted with a phosphate buffer. The tumor size was measured with a caliper, and the calculation formula was: $(length \times width)^2/2$.

(8) Drug Distribution Test of Recombinant Proteins in Tumor Tissues

The recombinant TRAIL and the TRAIL variant protein were labeled with a radioisotope of iodine ($^{125}I$) using a labeling kit (Pierce Corp.). The labeling results were as follows: the specific activity of $^{125}I$-TRAIL was 7.86 μCi/μg protein, and the specific activity of $^{125}I$-TRAIL variant was 7.49 μCi/μg protein. After the nude mice were inoculated with COLO-205 colon cancer, and when the tumor size reached 400-500 mm3, they were randomly grouped into wild-type and variant group. Each group included five time points: 5 min, 30 min, 60 min, 120 min and 240 min, and each time point included three animals. Each tumor-bearing nude mouse was injected with 100 μl of liquid containing 5 μl of protein. At each time point, the mice were sacrificed, the tumors were dissected by surgery, and the radiation dose was measured through a liquid scintillation counter. The distribution of recombinant TRAIL and the TRAIL variant protein in the tumor tissue should be represented by the radiation percentage contained in each gram of tissue (relative to the original injection of radioactive counting percentage) (% ID/g).

(9) In Vivo Binding Capability Test of Recombinant Proteins in the Body and Tumor Tissues The TRAIL, the TRAIL fusion protein, and bovine serum albumin were labeled with green fluorescein. The labeled protein was removed from the free fluorescein with a Sephadex-G25 size exclusion column. When the tumor grew to 400-500 mm3, 500 μg of fluorescent-labeled protein was injected through the tail veins of the tumor-bearing mice. After 30 min, the mice were sacrificed to remove the tumor, single-cell suspensions of tumor cells were prepared, and washed with normal saline several times. 60,000 cells were analyzed through a cell flow cytometer to compare the binding capability of the recombinant proteins on the tumor cell surfaces.

(10) Statistical Analysis

The statistical data analysis was carried out with social scientific data software. All tests should be repeated three times. The cell apoptosis and adhesion test results were represented with average standard deviation. The tumor size was represented by the standard error. If the P value was less than 0.05, it was regarded as a significant difference, and if it was less than 0.01, it was regarded as an extremely significant difference, indicated by * and ** respectively.

Figure 1:
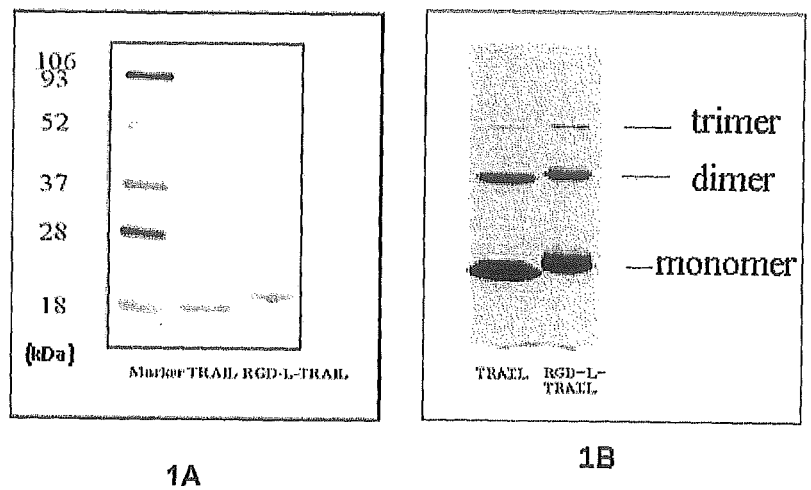
FIG. 1 The purified recombinant human TRAIL and its variant.

In previous reports, when the wild-type TRAIL was expressed in $E.$ $coli$, it would exist in the inactive inclusion body; in this invention, the TRAIL variant was combined with 4 cysteines (i.e. added with two pairs of disulfide bonds). When the variant was expressed in $E.$ $coli$, it would more easily form the inclusion body product without biological activity than wild-type TRAIL, and the purification became more difficult. In the present invention, by optimizing the expression conditions and the separation and purification processes, soluble forms of TRAIL and its variant were successfully realized. In addition, highly pure TRAIL and its variant proteins with full biological activity were obtained through utilization of a nickel metal affinity column and cation resin purification, with a yield of 60 mg/L. The expression products can be demonstrated under 15% denaturation and reducing conditions through silver-stained polyacrylamide gel electrophoresis analysis and mass spectrometry sequencing analysis (FIG. 1A). Also, under the expression conditions and purification process, TRAIL and its variants have a very high proportion of polymerized forms, which were very rare in previous methods of TRAIL expression and purification.

The tumor necrosis factor super-family proteins, including TRAIL can exist in monomer, dimer and trimer forms, and their biological activity depends on the dimer and trimer forms. To test whether fusion of the ACDCRGDCFC (SEQ ID NO:1) domain has an impact on the formation of TRAIL and TRAIL fusion protein variant polymers, a non-denaturing non-reducing polyacrylamide gel electrophoresis analysis was carried out, which showed that; the recombinant TRAIL and its variant proteins have the ability to form polymers. The results showed that there were three bands with molecular weights of about 20,000, 40,000 and 60,000 daltons for both TRAIL and its variant protein, which respectively were monomer, dimer and trimer (FIG. 1B). More important, the proportions of monomers, dimers and trimers of TRAIL and its variant proteins was basically the same. This demonstrated that the expressed and purified TRAIL and its variant proteins indeed have correct spatial conformation structure, and have higher biological activity than the TRAIL expressed in $E.$ $coli$ reported previously.

ACDCRGDCFC (SEQ ID NO:1) is the ligand of αVβ3 and αVβ5 integrins containing an RGD sequences, and having a ring cake or kringle-like structure that can form two pairs of disulfide bonds, which gives it better affinity and selectivity for integrins αVβ3 and αVβ5 than simple RGD sequences. In the present invention, the results showed that human foreskin microvascular endothelial cells do not adhere to the culture plate wells coated with TRAIL, but the human foreskin microvascular endothelial cells did adhere to the culture plate wells coated with TRAIL variant protein fused with αVβ3 and αVβ5 integrin ligands in a dose-dependent manner (FIG. 2). This indicated that the fusion of the short peptide ligand of integrins αVβ3 and αVβ5 in the TRAIL variant endowed TRAIL with the ability to adhere to endothelial cells by the cell's adhesion to culture wells.

Free RGD-L-TRAIL, RGD-L-TRAIL (C230G) (a kind of TRAIL variant fused with αVβ3 and αVβ5 integrin ligands together with a mutation at TRAIL's activity center causing TRAIL to lose its biological activity) and TRAIL protein were added to the culture plates coated with TRAIL variant protein for a competitive test. The test results showed that, free RGD-L-TRAIL or RGD-L-TRAIL (C230G) protein could significantly reduce the quantity of human foreskin microvascular endothelial cell which adhered to the microplates coated with RGD-L-TRAIL, but TRAIL has no such ability.

In the present invention, the integrin αVβ3 and αVβ5 receptors are the designed targets. We first conducted an analysis of the expression of integrins αVβ3 and αVβ5 on the surface of endothelial cells and tumor cells. The analysis results through a flow cytometer showed that the expression level of integrins αVβ3 and αVβ5 is greater on human foreskin microvascular endothelial cell surfaces; in addition, it should be noted that a variety of tumor cells have different degrees of expression of αVβ3 and αVβ5 integrins. Specifically, T lymphoma cells have a moderate abundance of αVβ3 and αVβ5 integrins; COLO-205 colon cancer cells have a relatively weak expression of the αVβ3 integrin, but the level of αVβ5 integrin was relatively higher; and there-was no expression of the αVβ3 integrin and a lower level of expression of the αVβ5 integrin in the MDA-231 breast cancer cells.

We also further evaluated the capacity of fluorescein-labeled TRAIL and its variant to directly bind with human foreskin microvascular endothelial cells. The results of flow cytometry showed that the TRAIL variant's binding capacity with human foreskin microvascular endothelial cells is much higher than that of wild-type TRAIL. These results revealed that the αVβ3 and αVβ5 integrin ligand short peptide can significantly enhance the specific binding capacity of the TRAIL fusion protein variant for the vascular endothelial cells.

We also evaluated the binding capacity of TRAIL and its variant to tumor cells in the tumor-bearing nude mice. The fluorescein-labeled TRAIL and its variant, and the negative control of bovine serum albumin were injected to tumor-bearing mice which were inoculated with COLO-205 tumor cells. 30 min later, the mice were sacrificed, the tumors were removed, and the binding capacity of the fluorescein-labeled TRAIL and its variants with the tumor cells was analyzed (FIG. 3). The results showed that the TRAIL fusion protein variant has a stronger binding capacity for the tumor cells than the wild-type TRAIL. These results confirmed that the αVβ3 and αVβ5 integrins short peptide ligand endowed the TRAIL fusion protein variant with the ability to selectively bind to tumor tissues, and enhanced its tumor-targeting ability.

We used COLO-205, Jurkat, and MDA-MB-231 tumor cells to evaluate the activity of TRAIL variant to induce tumor cell apoptosis. The tumor cells, after a series of concentration gradients of TRAIL variant or TRAIL-induced treatment, were analyzed by the Annexin V-FITC and PI double staining method with a flow cytometer. The results showed that, compared with TRAIL, the TRAIL fusion protein variants have stronger apoptosis-inducing properties in the COLO-205 colon cancer cells and Jurkat T lymphoma cells; however, in the MDA-MB-231 breast cancer cells, the ability of TRAIL variant to induce cell apoptosis only was slightly stronger than that of wild-type TRAIL. For example, for COLO-205 cells, the 2.43 ng/ml TRAIL-induced apoptosis rate was 43.7%; while TRAIL variant with the same dose could achieve an apoptosis rate as high as 87.5% (FIG. 4). The medial lethal dose of TRAIL on COLO-205, Jurkat and MDA-MB-231 were 3.5, 6.7 and 2.3 ng/ml respectively; while the corresponding medial lethal dose of TRAIL variant was reduced to 0.37, 0.41 and 1.2 ng/ml. For COLO-205, Jurkat, and MDA-MB-231 cells, the medial lethal dose of TRAIL variant was reduced by 9.5, 16.34, and 1.9 times respectively (FIG. 5). TRAIL variant has a better ability to induce apoptosis of tumor cells.

Because of the increased αVβ5 for αVβ3 integrin expression on tumor cells, the TRAIL fusion protein variant can specifically target and be delivered to the tumor cell and tumor blood vessel cell surfaces. In the present invention, the TRAIL fusion protein variant could significantly enhance tumor-targeting cell apoptosis. In COLO-205 and Jurkat tumor cells, the TRAIL variant's ability to induce apoptosis was 8-10 times greater than that of wild-type TRAIL or RGE-L-TRAIL (FIG. 5). Such enhanced activity could be attributed to the selective binding of the αV-β3 and αVβ5 integrin ligand domain to the integrin receptors. This selectivity enhanced the local concentration of the TRAIL variant, giving the TRAIL variant molecules greater access to TRAIL receptors, thus enhancing the signals to activate the cell apoptosis pathway. Such enhanced apoptosis activity is dependant on the abundance of αVβ3 and αVβ5 integrins-on the tumor cell surfaces. The greater the abundance of αVβ3 and αVβ5 integrins, the greater the enhancement of apoptosis activity. For instance, due to the relatively low integrin expression on the MDA-MB-231 cells, its apoptosis inducing activity was only increased by two times (FIG. 5). When the COLO-205 colon cancer cells were pre-incubated first with the competitive inhibitor RGD-L-TRAIL (C230G), which has an intact ACDCRGDCFC (SEQ ID NO:1) domain and a mutated TRAIL activity center, and then induced with RGD-L-TRAIL, the results revealed that the RGD-L-TRAIL-induced apoptosis activity declined significantly. The above results clearly indicate that the enhanced activity of TRAIL variant RGD-L-TRAIL was due to the targeting of ACD-CRGDCFC (SEQ ID NO:1). The tracking of the fluorescein-labeled TRAIL binding with the microvascular endothelial cells also demonstrated that TRAIL variant RGD-L-TRAIL has a very high affinity for microvascular endothelial cells. However, the binding of the TRAIL with the microvascular endothelial cells was very weak. The in vivo fluoresce in labeled and isotope-labeled test results further confirmed that TRAIL variant could be specifically concentrated on the tumor tissues.

The ACDCRGDCFC (SEQ ID NO:1) domain of the TRAIL variant was mutated to ACDCRGECFC (SEQ ID NO:2) (RGE-L-TRAIL variant), and the RGE-L-TRAIL variant protein had lost the ability to bind with the αVβ5 and αVβ3 integrins. The test results showed that, there was nearly no difference in activity between RGE-L-TRAIL and wild-type TRAIL, but it was much lower than that of RGD-L-TRAIL.

Different from the tumor cells, the normal human foreskin microvascular endothelial cells, 293T kidney cells and primary liver cells were treated with 300 ng/ml of the TRAIL variants or TRAIL for 24 hours. No obvious cell toxicity could be observed, which indicated that the TRAIL variants could distinguish the normal cells from tumor cells, and could induce tumor cell apoptosis with relative safety for the normal cells.

The fluorescence detection method was used to test the activity of Caspase-8 and Caspase-3 in the Jurkat cells after treatment of TRAIL and TRAIL variants. After two hours of treatment, compared with the same dose of TRAIL, the TRAIL variant could induce 2.5 times higher caspase-8 and caspase-3 activity as that of the wild-type TRAIL. Among the FADD$^{-/-}$ and Caspase-8$^{-/-}$ deficient Jurkat cells, no induced cell apoptosis could be accomplished for the TRAIL and TRAIL variants; which suggested that TRAIL variant induces apoptosis through the death receptor --FADD--Caspase-8 pathway, the same as wild-type TRAIL.

Two kinds of colon cancer models, COLO-205 and HT-29, were used to test the anti-tumor activity of the TRAIL variant in the athymic nude mice. Because COLO-205 colon cancer cells were sensitive to TRAIL, the therapeutic effect of separate use of TRAIL and TRAIL variant was assessed on this model. On the 8th day after the nude mice were inoculated with tumor cells, administration of drugs through the tail vein began for ten days in succession. The mice were divided into four groups; 100 μg TRAIL variant group, 20 μg TRAIL variant group, 100 μg wild-type TRAIL group, and PBS control group. The statistical data showed that compared with the PBS control group, 100 μg of wild-type TRAIL would cause mild tumor shrinkage, and on the 37$^{th}$ day, the tumor inhibition rate was 37% (P=0.08). However, in the 100 μg TRAIL variant group, the growth of tumor was significantly inhibited, particularly obvious during the treatment period, on the 19$^{th}$ day, the tumor inhibition rate was 70.4% (P=0.002), and on the 37$^{th}$ day, the tumor inhibition rate was 56.8% (P=0.016). Moreover, the TRAIL variant's inhibition of tumor growth was dose-dependent. In the 20 μg TRAIL variant group, the tumor inhibition rate was 37.1% (37 days, P=0.045), slightly more than 5 times that the 100 μg dose wild-type TRAIL group.

The invention also provides the anti-tumor effect of combined use of TRAIL variant and chemotherapeutic drug CPT-11. Protein injection was carried out by intraperitoneal injection once a day for TRAIL or TRAIL variant, for two weeks total, and intravenous injection once every two days from CPT-11 via tail veins, seven times in total. In the combined drug administration group, for the COLO-205 tumor models sensitive to TRAIL, a relatively low dose of CPT-11 (6.25 mg/kg/each) combined with different doses of RGD-L-TRAIL (100 μg/day/each, or 30 μg/day/each), or TRAIL (270 μg/day/each, or 90 μg/day/each) was selected. Among the HT-29 colon cancer models resistant to TRAIL, a relatively higher dose of CPT (25 mg/kg/each time) combined with RGD-L-TRAIL 200 µg/day/each or TRAIL 400 µg/day/each was selected. As shown in the Figures, among the COLO-205 tumor models, compared with PBS control groups, individual injection of low dose of CPT-11 could slightly inhibit the tumor growth. However, this dose of CPT-11 combined 100 µg RGD-L-TRAIL has a significant tumor inhibition effect (96.2%, P=0.0001, 36 days). This effect was even better than the higher dose of the TRAIL+CPT-11 combined treatment group (270 µm/day/each) (89%, P=0.001, 36 days). Similarly, the tumor inhibition rate of 30 µg/day/each RGD-L-TRAIL group 77.1%, P=0.005, 36 days was higher than the 90 µg/day/each dose of TRAIL group (67.8%, P=0.012, 36 days). It is worth mentioning that in the 100 µg/day/each dose of RGD-L-TRAIL+CPT-11 combined treatment group, after 36 days, among the 10 mice receiving drug administration, the tumors of 8 mice disappeared; and among the ten animal treatment groups receiving 270 µg/day/each TRAIL+CPT-11, the tumors disappeared for 6 mice. The curative effect of the 100 µg/day/per dose of RGD-L-TRAIL+CPT-11 combined treatment group was better than that of the 270 µg/day/each TRAIL+CPT-11 combined treatment group.

Among the TRAIL-resistant HT-29 colon cancer models, when RGD-L-TRAIL was used separately, even when the daily intraperitoneal injection was 400 µg/each nude mouse, only a mild anti-tumor effect was observed. However, for the combined treatment with RGD-TRAIL+CPT-11, it could significantly inhibit the tumor growth, and presented better than the TRAIL+CPT-11 combined treatment effect. The group of 200 µg RGD-TRAIL plus 25 mg/kg CPT-11 combined treatment presented a better anti-tumor effect than that of the 400 µg TRAIL and 25 mg/kg CPT-11 combined treatment group. This showed that, to achieve the same treatment effect, the dose required for the TRAIL variant was far less than that of the wild-type TRAIL. Therefore, our results demonstrated that, the fusion of αV-β3 and αVβ5 integrin short peptide ligand ACDCRGDCFC (SEQ ID NO:1) to TRAIL significantly enhanced its in vivo anti-tumor activity.

The in vivo animal model test further demonstrated that the TRAIL variant has a better curative effect than that of wild-type TRAIL. Among the COLO-205 tumor models, the same dose of the TRAIL variant has a significantly higher anti-tumor effect than that of the wild-type TRAIL. Even when the dose of the TRAIL variant is ⅕ of the dose of the wild-type TRAIL, its tumor inhibition rate is basically the same; which indicated that after fusion of TRAIL and the tumor-targeting peptide, the in vivo level of anti-tumor biological activity was enhanced on the animal tumor models. Similarly, the drug efficacy of the TRAIL variant was enhanced when used individually, and when used in combination with the chemotherapy drug CPT-11, it also has obvious synergistic effect, with even more significant curative effect. Combined use of the TRAIL variant and CPT-11 can not only reduce the required dose and minimize the potential systemic toxicity, but also can expand to the treatment of tumors not sensitive to TRAIL. In the TRAIL-sensitive COLO-205 models, low dose of TRAIL variant (100 µg/day/each) combined with low dose of CPT-11 (6.25 mg/kg body weight) could extremely significantly inhibit tumor growth and cause tumor recession, or even cause some of the tumors to disappear completely. To achieve the same therapeutic effect with the combined treatment program for the COLO-205 models, the dose required for the wild-type TRAIL is 3-9 times of that of TRAIL variant. For the TRAIL-insensitive HT-29 model, the dose required for the wild-type TRAIL is at least 2 times higher than that of the TRAIL variant. The in vivo animal test fully demonstrated that the therapeutic effect of TRAIL variant is better than that of TRAIL.

In order to confirm that the increased anti-tumor activity of TRAIL variant on animal models results from targeting concentration on the tumor tissues, we detected the distribution of I-125 isotope-labeled TRAIL variant RGD-TRAIL in the tumor tissues. The same radiation dose of I-125 labeled TRAIL and its variant were separately injected to COLO-205 tumor-bearing nude mice; 5, 30, 60, 120 and 240 minutes later, the mice were sacrificed to remove the tumor tissues and weigh them, then the isotope dose was measured in the liquid scintillation counter. The results showed that after fusion of TRAIL with the aV-β3 and αVβ5 integrin short peptide ligand ACDCRGDCFC (SEQ ID NO:1), the concentration of TRAIL proteins on COLO-205 tumor tissue regions was obviously enhanced. During the initial injection period, the distribution of $^{125}$I-RGD-L-TRAIL in the tumor tissues was about twice that of $^{125}$I-TRAIL. Due to the increased affinity of RGD-L-TRAIL for the tumor tissues, and the increased distribution in tumor tissues, its clearing speed in the circulating blood was significantly reduced, thus prolonging its distribution in the tumor tissues. 240 minutes after injection, it is difficult to detect wild-type TRAIL in the tumor tissues, however, there was still a continuous distribution of RGD-L-TRAIL in the tumor area. Therefore, the increased distribution of TRAIL variant in the tumor tissue areas and the enhanced anti-tumor activity on the animal models fully demonstrated that the TRAIL variant can endow TRAIL with better tumor targeting, and could enhance the anti-tumor effect while reducing the drug dose.

In the present invention, a method for improving the curative effect of TRAIL on tumors was provided, that is, the fusion of TRAIL and αVβ5 and αV-β3 integrin ligands could realize the direct delivery of TRAIL to the tumor area, and obviously enhance its anti-tumor effect. In addition, it could reduce the dose of protein required for the same curative effect, enhance its bioavailability, reduce treatment costs, and ultimately reduce and overcome the systemic side effect of TRAIL, presenting good application prospects in the area of tumor treatment.

The invention claimed is:

1. A method for making a fusion protein comprised of an integrin ligand of SEQ ID NO: 1, a tumor necrosis factor related apoptosis inducing ligand (TRAIL) and a linking peptide connecting the TRAIL to the integrin ligand, the method comprising the steps of:
constructing a polynucleotide encoding the fusion protein by performing a PCR reaction including a first PCR primer of SEQ ID NO: 3 and a second PCR primer of SEQ ID NO: 4; the polynucleotide comprising a gene for the TRAIL fused with the linking peptide and the integrin ligand of SEQ. ID NO:1;

expressing the polynucleotide in *E. coli;* cultivating the *E. coli*, wherein the cultivated *E. coli* produces the fusion protein without forming an inclusion body product;

separating the cultivated *E. coli* from the fusion protein; and purifying the fusion protein.

2. The method of claim 1, wherein the step of purifying the fusion protein is performed by metal affinity chromatography and ion-exchange chromatography.

3. The method of claim 1, wherein the *E. coli* is *Escherichia coli* BL21.

4. The method of claim 1, wherein the step of cultivating the *E. coli* occurs at 37° C. for 2.5 hours and subsequently for 1-2 hours at 24° C.

5. The method of claim 1, wherein the step of separating the *E. coli* from the fusion protein is performed by suspending the *E. coli* in a lysis buffer and lysing the *E. coli* through ultrasonication.

* * * * *

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: Proapoptotic Peptide
<220> FEATURE:
<221> NAME/KEY: BINDING
<222> LOCATION: (1)..(10)
```

-continued

```
<400> SEQUENCE: 1

Ala Cys Asp Cys Arg Gly Asp Cys Phe Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Proapoptotic Peptide
<220> FEATURE:
<221> NAME/KEY: BINDING
<222> LOCATION: (1)..(10)

<400> SEQUENCE: 2

Ala Cys Asp Cys Arg Gly Glu Cys Phe Cys
1               5                   10

<210> SEQ ID NO 3
<211> LENGTH: 79
<212> TYPE: DNA
<213> ORGANISM: Artificial Sequence
<220> FEATURE:
<223> OTHER INFORMATION: PCR Primer
<220> FEATURE:
<221> NAME/KEY: primer_bind
<222> LOCATION: (1)..(78)

<400> SEQUENCE: 3
tgcagatcat atggcatgcg actgccgtgg tgactgcttc tgcggtggtg gtggtggtgt     60
gagagaaaga ggtcctcag                                                  79

<210> SEQ ID NO 4
<211> LENGTH: 28
<212> TYPE: DNA
<213> ORGANISM: Artificial Sequence
<220> FEATURE:
<223> OTHER INFORMATION: PCR Primer
<220> FEATURE:
<221> NAME/KEY: primer_bind
<222> LOCATION: (1)..(28)

<400> SEQUENCE: 4
atggatcctt agccaactaa aaaggccc                                        28
```